US011517517B2

(12) United States Patent
Patil et al.

(10) Patent No.: US 11,517,517 B2
(45) Date of Patent: Dec. 6, 2022

(54) COMPOSITION COMPRISING A STRUCTURED AQUEOUS PHASE AND SERICIN

(71) Applicant: Conopco, Inc., Englewood Cliffs, NJ (US)

(72) Inventors: Nivedita Jagdish Patil, Bangalore (IN); Siva Rama Krishna Perala, Bangalore (IN); Janhavi Sanjay Raut, Bangalore (IN); Jyoti Kumar Tiwari, Bangalore (IN)

(73) Assignee: Conopco, Inc., Englewood Cliffs, NJ (US)

( * ) Notice: Subject to any disclaimer, the term of this patent is extended or adjusted under 35 U.S.C. 154(b) by 244 days.

(21) Appl. No.: 16/757,729

(22) PCT Filed: Oct. 9, 2018

(86) PCT No.: PCT/EP2018/077417
§ 371 (c)(1),
(2) Date: Apr. 20, 2020

(87) PCT Pub. No.: WO2019/081196
PCT Pub. Date: May 2, 2019

(65) Prior Publication Data
US 2021/0186843 A1 Jun. 24, 2021

(30) Foreign Application Priority Data
Oct. 25, 2017 (EP) .................................. 17198217

(51) Int. Cl.
| | | |
|---|---|---|
| *A61K 8/64* | (2006.01) | |
| *A61K 8/04* | (2006.01) | |
| *A61K 8/19* | (2006.01) | |
| *A61K 8/27* | (2006.01) | |
| *A61Q 19/00* | (2006.01) | |

(52) U.S. Cl.
CPC .............. *A61K 8/64* (2013.01); *A61K 8/042* (2013.01); *A61K 8/19* (2013.01); *A61K 8/27* (2013.01); *A61Q 19/00* (2013.01); *A61K 2800/48* (2013.01); *A61K 2800/58* (2013.01)

(58) Field of Classification Search
CPC ...... A61K 8/042; A61K 8/64; A61K 2800/48; A61K 2800/58; A61K 8/19; A61K 8/27; A61K 8/365; A61K 8/987; A61K 8/02; A61Q 19/00; A61Q 5/06; A61Q 5/12; A61Q 19/10; A45D 7/04; A45D 7/06; C07K 14/43586
See application file for complete search history.

(56) References Cited

U.S. PATENT DOCUMENTS

| | | | |
|---|---|---|---|
| 2005/0130857 A1* | 6/2005 | Meesilpa | A61K 8/987 510/141 |
| 2007/0087024 A1 | 4/2007 | Knight | |
| 2009/0176965 A1 | 7/2009 | Lee et al. | |
| 2016/0136241 A1 | 5/2016 | Wang et al. | |

FOREIGN PATENT DOCUMENTS

| | | | |
|---|---|---|---|
| CN | 102775465 | 11/2012 | |
| CN | 103774246 | 5/2014 | |
| EP | 0154303 | 9/1985 | |
| EP | 0841065 | 5/1998 | |
| EP | 1731556 | 12/2006 | |
| EP | 2865442 | 4/2015 | |
| GB | 888625 | 1/1962 | |
| JP | 2001039999 | 2/2001 | |
| JP | 2006111667 | 4/2006 | |
| JP | 1731556 A1 * | 12/2006 | ............... C08J 9/28 |
| KR | 20150046915 | 5/2015 | |

OTHER PUBLICATIONS

Aramwit, et al. ; Monitoring of inflammatory mediators induced by silk sericin; J. Biosci. Bioeng.; 2009; pp. 556-561; 105(5).
Kitisin, et al, ; Characterization of Silk Sericin as an Anti-Aging Agent; J. of Agricultural Science; 2013; pp. 54-62; 5(3).
V. R. Silva et al., ; High Molecular weight sericin obtained by high temperature and ultrafiltration process; Procedia Engineering; 2012; pp. 833-841; 42.
Teramote et al.,; Preparation of Elastic Silk Sericin Hydrogel; Biosci. Biotechnol. Biochem., ; 2005; pp. 845-847; vol. 69(4).
Yoon Nam Jo, et al,; Effects of solvent on the solution properties, structural characteristics and properties of silk sericin; Intl. J. Biol. Macromolecules; 2015; pp. 287-295; vol. 78.
Teamoto, et al.; Analysis of Structural Properties and Formation of Sericin Fiber by Infrared Spectroscopy; J. of inset Biotechnology and Seriology; 2003; pp. 157-162; 72.
Wilson, et al.; Conformational Transitions in Model Silk Peptides; Biophyscial J.; 2000; pp. 2690-2701; 78.
Teramoto et al.; Preparation of Gel Film from Bombyx mori Silk Sericin and Its Characterizastion as a Wound Dressing; Biosci. Biotechnol. Biochem. ; 2008; pp. 3189-3196; 72 (12).

(Continued)

*Primary Examiner* — Audrea B Coniglio
(74) *Attorney, Agent, or Firm* — Stephanie S. DelPonte

(57) ABSTRACT

The invention relates to a composition comprising 5 to 100 wt. % of a structured aqueous phase wherein the composition contains 0.1 to 10 wt. % sericin by weight of water, said sericin having a proportion of beta-sheet in the secondary structure that exceeds 80%. It was found that sericin having a proportion of beta-sheet in the secondary structure that exceeds 80% is an excellent water structurant and can suitably be used to structure the aqueous phase of a wide range of products, such as cosmetic products, pharmaceutical products, food products and detergent compositions.

13 Claims, No Drawings

(56) References Cited

OTHER PUBLICATIONS

Dash et al.; Isolation, purification and characterization of silk protein sericin from cocoon peduncles of tropical tasar silkworm, *Antheracea mylitta*; International Journal of Biological Macromolecules; 2006; pp. 255-258; XP27949897; vol. 38.
IPRP2 in PCTEP2018077417; Sep. 24. 2019.
Search Report and Written Opinion in EP17198217; dated Dec. 11, 2017.
Search Report and Written Opinion in PCTEP2018077417; dated Dec. 5, 2018.
Huang et al.; Cloning, Expression, and Assembly of Sericin-like Protein; The Journal of Biological Chemistry; 2003; pp. 46117-46123; XP55430155; vol. 278 No. 46.
Padamwar et al.; Silk sericin and its applications: A review; Journal of Scientific & Industrial Research; 2004; pp. 323-329; 63.
IPRP2 in PCTEP2018080472; Jan. 31, 2020.
Voegeli et al., ; Sericin Silk Protein: Unique Structure and Properites; Cosmeics & Toilletries; 1993; pp. 101-108, XP9504839; 108, No. 12; Retrived from the Internet; Switzerland.
Search Report and Written Opinion in PCTEP2018080472; dated Feb. 19, 2019.
Search Report and Written Opinion in EP17208941; dated May 9, 2018.
Chirila, T.V., et al., "Further development of silk sericin as a biomaterial: comparative investigation of the procedures for its isolation from Bombyx mori silk cocoons", Prog. Biomater, 5, pp. 135-145 (2016).
Gimenes, M., et al., "High Molecular Sericin from Bombyx mori Cocoons: Extraction and Recovering by Ultrafiltration", Intl. Journal of Chemical Engineering and Applications, 5(3), pp. 266-271 (2014).

Kataoka, K., et al., "On the solubility of sericin in water", J. Sericult. Sci. Jpn., 46(3), pp. 227-230 (1977).
Kelly, S., et al., "How to study proteins by circular dichroism", Biochimica et Biophysica Acta, 1751, pp. 119-139 (2005).
Oh, H., et al., " Refining hot-water extracted silk sericin by ethanol-induced precipitation", Int. J. Biol. Macromol, 48, pp. 32-37 (2011).
Teramoto, H. et al., "Role of hydroxyl side chains in Bombyx mori silk sericin in stabilizing its solid structure", Macromolecules, 40, pp. 1562-1569 (2007).
Yang, M., et al., "Tuning molecular weights of Bombyx mori (B. mori) silk sericin to modify its assembly structures and materials formation", ACS Appl. Mater. Interfaces, 6, pp. 13782-13789 (2014).
Yazawa, K., et al., "Influence of water content on the p. sheet formation, thermal stability, water removal, and mechanical properties of silk materials", Biomacromolecules, 17, pp. 1057-1066 (2016).
Zhang, X., et al., "Fabrication of silk sericin nanofibers from a silk sericin-hope cocoon with electrospinning method", International Journal of Biological Macromolecules, 50, pp. 337-347 (2012).
Gupta, D., et al., "Extraction and characterization of silk sericin", Indian Journal of Fibre & Textile Research, 39, pp. 364-372 (2014).
Gupta, D., et al., "Cleaner process for extraction of sericin using infrared", Journal of Cleaner Production, 52, pp. 488-494 (2013).
Liangjun, Z., et al., "Structure transformation of sericin protein dissolved from cocoon layer in hot water", Zhejiang Nongye Daxue Xuebao, 24(3), 1 page (1998).

* cited by examiner

COMPOSITION COMPRISING A STRUCTURED AQUEOUS PHASE AND SERICIN

FIELD OF THE INVENTION

The present invention relates to compositions that comprise a structured aqueous phase and 0.1 to 10 wt. % sericin by weight of water, said sericin having a proportion of beta-sheet in the secondary structure that exceeds 80%.

BACKGROUND OF THE INVENTION

In water-based cosmetic, pharmaceutical, tissue engineering, detergents and food formulations there is a need to control the rheological properties of the formulation to ensure the formulation has the desired feel, appearance, viscosity etc. A water structurant is an ingredient that is applied in the aqueous phase of such formulations to modulate the rheological properties. Depending on the nature of the water structurant, the composition of the aqueous and the concentration of the water structurant applied, these rheological properties can vary widely.

Sericin, a component of silk, is a protein that can act as a water structurant. Silk is a natural protein fibre derived from the silkworm Bombyx mori and is typically composed of two proteins fibroin (70 to 80%) and sericin (20 to 30%), the remainder being a mixture of wax, carbohydrate and inorganic matter. Fibroin is a fibrous glycoprotein, present as a delicate twin thread, enveloped by layers of sericin that help in the formation of a cocoon. To manufacture silk from the dried cocoons of silkworm, fibroin is separated from sericin by a so-called 'degumming' process and sericin is discarded in the wastewater. Degumming by heat or heat under pressure has an advantage because it results in fewer impurities. Many industrial removal methods involve extraction with soaps and detergents, enzymatic hydrolysis, acid or alkaline hydrolysis.

Until recently, sericin was seen as a waste product from silk production. Sericin exists in a wide range of molecular weights, from 10 to over 400 kDa. Sericin occurs mostly in amorphous random coil and to a lesser extent in a beta-sheet structure (Padamwar et al., Silk sericin and its applications: A review, Journal of Scientific & Industrial Research, 2004, 63, pp 323-329).

US 2009/176965 discloses that the molecular structure of isolated sericin can be modified by irradiating a sericin solution to produce high molecular weight sericin having improved radical scavenging ability and Tyrosinase inhibitory ability. A maximum of 50% beta-sheet structure is obtained (FIG. 2, 200 kGy dose radiation). Sericin having modified molecular structure can be used in manufacturing a variety of products for improvement of antioxidant and tyrosinase inhibitory abilities, which include food products, cosmetics and/or pharmaceutical products and medicines.

JP 2006111667 discloses a method for production of sericin hydrogel. A silk extract having a molecular weight greater than 50 kDa is provided, to which alcohol is added and the mixture allowed to stand. The sericin in a sericin aqueous solution shows absorption to 1641 $cm^{-1}$ which belongs to random structure in an amide absorption band. On the other hand, sericin hydro-gel shows absorption to 1620 $cm^{-1}$ which belongs to beta-sheet structure in an amide I absorption band. Addition of ethanol stimulating formation of the hydrogen bond between sericin molecules, and a three-dimensional network arising as a result, forms a sericin hydro-gel.

US 2016/0136241 discloses a sericin hydrogel. The cocoons of fibroin-deficient mutant silkworm, Bombyx mori, are utilized as the raw material. A sericin solution is prepared by extraction and purification of the raw material and then crosslinked by a crosslinking agent (aldehydes and geniposide) to obtain the sericin hydrogel. The crosslinked sericin hydrogel maintained the natural conformation of the sericin.

SUMMARY OF THE INVENTION

The inventors have developed a method that enables the isolation of a sericin from silk having an extremely high proportion (>80%) of beta-sheet in the secondary structure. It has further been found that such a sericin is an excellent water structurant and can suitably be used to structure the aqueous phase of a wide range of products, such as cosmetic products, pharmaceutical products, food products and detergent compositions.

Thus, the present invention provides a composition comprising 5 to 100 wt. % of a structured aqueous phase wherein the composition contains 0.1 to 10 wt. % sericin by weight of water, said sericin having a proportion of beta-sheet in the secondary structure that exceeds 80%.

The sericin of the present invention, i.e. sericin having more than 80% beta-sheet structure, can be isolated from silkworm cocoons by a process that comprises the steps of:
cutting the cocoons in pieces of appr. 5×5 mm;
subjecting the cocoons to a first washing treatment with de-mineralized water (demi-water) at approximately 25° C.;
subjecting the cocoons to a second washing treatment with demi-water at approximately 70° C.;
subjecting the cocoons to a second washing treatment with ethanol at approximately 25° C.;
removing the ethanol from the washed cocoons by evaporation at a temperature below 30° C.;
combining 1 party by weight of the dry washed cocoons with approximately 20 parts by weight hot water (≈95° C.) to form an aqueous suspension;
keeping the aqueous suspension at a temperature of approximately 120° C. for about 5 minutes to about 20 minutes;
centrifugating the heated suspension at 4000 G for 20 minutes, followed by decanting to recover the sericin protein extract.

In the above process it is preferred that the aqueous suspension is kept at a temperature of approximately 120° C. for up to 15 minutes, preferably 10 minutes, and most preferably up to 5 minutes. The present inventors have determined that when the aqueous suspension is maintained at a temperature of approximately 120° C. for up to about 20 minutes, the sericin thus produced has a proportion of beta-sheet in the secondary structure that exceeds 80%. The amount of sericin in the beta sheet form reduces as the temperature is maintained for longer times.

In contrast to the prior art method described by US 2009/0176965, the high beta sheet sericin is readily usable, without using irradiation with gamma-ray, electron or X-ray radiation.

It has been found that rheological properties of the sericin structured aqueous phase of the present composition can be tuned by altering the pH and/or by adjusting the concentration of multivalent cations (e.g. $Zn^{2+}$, $Cu^{2+}$, $Ca^2$).

There is also provided a process of preparing the composition of the present invention, said process comprising:

providing an aqueous component containing sericin having a proportion of beta-sheet in the secondary structure that exceeds 80%; and mixing 100 parts by weight of the aqueous component with at least 5 parts by weight of one or more other components.

DETAILED DESCRIPTION OF THE INVENTION

As used herein the term "comprising" encompasses the terms "consisting essentially of" and "consisting of". Where the term "comprising" is used, the listed steps or options need not be exhaustive.

Unless otherwise specified, numerical ranges expressed in the format "from x to y" are understood to include x and y.

In specifying any range of values or amounts, any particular upper value or amount can be associated with any particular lower value or amount.

Except in the examples and comparative experiments, or where otherwise explicitly indicated, all numbers are to be understood as modified by the word "about".

All percentages and ratios contained herein are calculated by weight unless otherwise indicated.

As used herein, the indefinite article "a" or "an" and its corresponding definite article "the" means at least one, or one or more, unless specified otherwise.

The various features of the present invention referred to in individual sections above apply, as appropriate, to other sections mutatis mutandis. Consequently, features specified in one section may be combined with features specified in other sections as appropriate. Any section headings are added for convenience only, and are not intended to limit the disclosure in any way.

The invention is not limited to the embodiments illustrated in the drawings. Accordingly, it should be understood that where features mentioned in the claims are followed by reference numerals, such numerals are included solely for the purpose of enhancing the intelligibility of the claims and are in no way limiting to the scope of the claims.

The present invention relates to a composition comprising 5 to 100 wt. % of a structured aqueous phase wherein the composition contains 0.1 to 10 wt. % sericin by weight of water, said sericin having a proportion of beta-sheet in the secondary structure that exceeds 80%.

The term "structured aqueous phase", as used herein, unless indicated otherwise, refers to an aqueous phase that exhibits non-Newtonian behaviour due to the presence of one or more hydrocolloids.

The term "sericin" as used herein, unless indicated otherwise, refers to sericin polypeptide obtained from the *Bombyx mori* silkworm, said polypeptide having a molecular weight of at least 2 kDa. Sericin from *Bombyx mori* is identified by the UniProtKB database identifier P07856. The term "sericin" also encompasses partially hydrolysed forms of native sericin.

The term "secondary structure" as used herein, unless indicated otherwise, refers to the spatial arrangement of local segments of sericin polypeptides, denoted as alpha helix, beta-sheet or random coil.

The term "alpha helix" as used herein, unless indicated otherwise, refers to a portion of molecular structure that is a rodlike structure in which a tightly coiled backbone forms the inner part of the rod and the side chains extend outward in a helical array. The alpha helix is stabilized by hydrogen bonds between the NH and CO groups of the main chain. In particular, the CO group of each amino acid forms a hydrogen bond with the NH group of the amino acid that is situated four residues ahead (i+4) in the backbone sequence (Berg J M, Tymoczko J L, Stryer L., Biochemistry $5^{th}$ Ed. New York, W H Freeman, 2002, 3.3.1).

The term "beta-sheet" as used herein, unless indicated otherwise, refers to a portion of molecular structure formed by linking two or more beta-strands by hydrogen bonds. A beta-strand is a stretch of polypeptide chain typically 3 to 10 amino acids long with backbone in an extended conformation. Adjacent chains in a beta-sheet can run in opposite directions (antiparallel β sheet) or in the same direction (parallel β sheet). In the antiparallel arrangement, the NH group and the CO group of each amino acid are respectively hydrogen bonded to the CO group and the NH group of a partner on the adjacent chain in the parallel arrangement, the hydrogen-bonding scheme is more complicated. For each amino acid, the NH group is hydrogen bonded to the CO group of one amino acid on the adjacent strand, whereas the CO group is hydrogen bonded to the NH group on the amino acid two residues farther along the chain (Berg J M, Tymoczko J L, Stryer L., Biochemistry $5^{th}$ Ed. New York, W H Freeman, 2002, 3.3.2).

The term "random coil" as used herein, unless indicated otherwise, refers to a portion of molecular structure lacking a defined hydrogen bonding pattern such as alpha helix or beta-sheet.

The sericin secondary structure can be assigned using circular dichroism spectroscopy in the "far-UV" spectral region (190 to 250 nm). At these wavelengths, the chromophore is the peptide bond, and the signal arises when it is located in a regular, folded environment. A maximum ellipticity per residue (theta) at circa 195 nm and a minimum at circa 220 nm is characteristic of a beta-sheet structure. A maximum ellipticity per residue (theta) at circa 190 nm and double minima at circa 205 nm and 225 nm is characteristic of alpha helix. A minimum ellipticity at circa 200 nm and a broad maximum between 210 and 220 nm is characteristic of a random coil structure.

In accordance with a particularly preferred embodiment, the sericin in the composition of the present invention has a proportion of beta-sheet in the secondary structure that exceeds 80%, even more exceeds 85% and most preferably exceeds 90%.

In one preferred embodiment, the sericin has a molecular weight of in the range of 2 kDa to 400 kDa, preferably in the range 25 kDa to 300 kDa, more preferably 40 kDa to 250 kDa, even more preferably in the range 60 to 200 kDda.

In a preferred embodiment of the invention the composition contains 0.2 to 4 wt. % sericin by weight of water. Preferably the composition contains 0.3 to 3 wt. % sericin by weight of water, more preferably 0.4 to 2 wt. % sericin by weight of water.

Preferably, at least 80 wt. % of the sericin contained in the composition is present in the structured aqueous phase. More preferably, at least 90 wt. % of the sericin, most preferably at least 95 wt. % of the sericin contained in the composition is present in the structured aqueous phase.

The inventors have discovered that the water structuring capability of the sericin is optimal when the structured aqueous phase has a pH in the range from 2.0 to 4.0 or from 5.5 to 10.5. Preferably, the structured aqueous phase has a pH in the range from 5.8 to 9.5, even more preferably in the range from 6 to 8.5.

The composition of the present invention can be provided in the form a single phase aqueous composition or in the form of a composition that comprises one or more additional distinct phases. Examples of such multiphase compositions are emulsions and suspensions. In accordance with a particularly preferred embodiment, the composition comprises 1 to 80 wt. %, more preferably 5 to 70 wt. %, most preferably 10 to 50 wt. % of one or more non-aqueous phases.

According to a particularly preferred embodiment, the structured aqueous phase is a continuous aqueous phase. The compositions comprising such a continuous structured aqueous phase preferably have a storage modulus (G') at 25° C. in the range of 50-3000 Pa, more preferably in the range of 100-2000 Pa, and most preferably 200 to 800 Pa. The loss modulus (G") of this composition preferably is in the range of 10 to 300 Pa, more preferably in the range of 20 to 200 Pa and most preferably in the range of 50 to 100 Pa.

Using oscillatory rheology, it is possible to quantify both the viscous-like and the elastic-like properties of a material at different time scales. The basic principle of an oscillatory rheometer is to induce a sinusoidal shear deformation in the sample and measure the resultant stress response; the time scale probed is determined by the frequency of oscillation, ω, of the shear deformation. A sample is placed between two plates. While the top plate remains stationary, a motor rotates the bottom plate, thereby imposing a time dependent strain $\gamma(t)=\gamma \cdot \sin(\omega t)$ on the sample. Simultaneously, the time dependent stress σ(t) is quantified by measuring the torque that the sample imposes on the top plate.

Both the storage modulus (G') and the loss modulus (G") of the fluid product are determined at 25° C. using an AR1000 Rheometer (TA Instruments), using cone-plate geometry, with a cone diameter of 40 mm, cone angle of 2°, and a truncation gap of 58 μm. The program settings applied are as follows:

- A stress τ is chosen in the Lineair Visco-elastic range of the product (LVER is determined by an Amplitude Sweep). The stress is kept constant at 1 Pa.
- An increasing ramp log of angular frequency ω is set on the sample from low to high frequency, starting at 6.28 rad/s. The end ω is 628.32 rad/s.
- The setting in which the measuring points are gathered is the 'no time settings'. In this modus the apparatus waits for a steady state situation before it takes his measuring point.
- Every decade 10 measuring points are taken.

In accordance with yet another preferred embodiment, the structured aqueous phase is a gelled aqueous phase that is structured by a three-dimensional network of hydrocolloid. The gelled aqueous phase may be gelled by a three-dimensional network that solely consists of sericin (sericin hydrogel) or, alternatively, it may comprise a three-dimensional network that also comprises other gelling agents.

The structured aqueous phase typically contains at least 50 wt. % water. Preferably, the structured aqueous phase contains at least 60 wt. % water, more preferably at least 70 wt. % water, even more preferably at least 80 wt. % water and most preferably at least 85 wt. % water.

According to a particularly preferred embodiment, the present composition is an emulsion comprising 1 to 80 wt. % of a hydrophobic phase and 20 to 99 wt. % of the structured aqueous phase. More preferably, the emulsion comprises 5 to 70 wt. % of the hydrophobic phase and 30 to 95 wt. % of the structured aqueous phase. Most preferably, the emulsion contains 10 to 50 wt. % of the hydrophobic phase and 50 to 90 w. % of the structured aqueous phase. Besides the hydrophobic phase and the structured aqueous phase, the emulsion composition may contain other phases, e.g. a dispersed phase consisting of small particles of solid material.

The inventors have found that the water structuring capability of sericin can be enhanced by the presence of multivalent metal cations. Consequently, in yet another preferred embodiment, the composition comprises at least 0.08 mmol of multivalent metal cation, said multivalent metal cation being selected from $Zn^{2+}$, $Cu^{2+}$, $Ca^{2+}$ and combinations thereof. More preferably, the composition comprises at least 0.1 mmol of said multivalent metal cation, even more preferably in the range of 0.2 to 0.9 mmol of said multivalent metal cation, more preferably 0.3 to 0.8 mmol of said multivalent metal cation and most preferably 0.4 to 0.6 mmol of said multivalent metal cation.

The sericin employed in accordance with the present invention preferably is a highly pure sericin quality. Accordingly, in another preferred embodiment, the present composition contains fibroin and sericin in a weight ratio of fibroin:sericin of not more than 1:5, preferably of not more than 1:10.

In a particularly preferred embodiment, the structured aqueous phase comprises a sericin hydrogel. It has been found that the sericin of the present invention forms a hydrogel without the need of additional hydrocolloids. Typically, the sericin contained in the composition is capable of forming a free-standing gel at a concentration of 1% sericin by weight of water. Even more preferably, said free standing gel has a storage modulus (G') at 25° C. of at least 200 Pa.

Unlike the sericins described in US 2016/036241, the sericin of the present invention is not a gluteraldehyde cross-linked sericin. Even more preferably, the sericin is not a cross-linked sericin.

Unlike the sericins described in US 2009/176965, the sericin of the present invention is not an irradiated sericin that has been subjected to radiation at an absorption dose of 10 kGy to 500 kGy.

The structured phase of the present composition preferably contains less than 0.1 wt. % ethanol, more preferably less than 0.01 wt. % ethanol.

In a particular embodiment, the present composition comprises at least 0.3% preferably at least 0.4% of sericin by weight of water. This sericin preferably has a molecular weight of at least 10 kDa and having a proportion of beta-sheet in the secondary structure that exceeds 80%.

In an even more preferred embodiment, the composition comprises at least 0.3% preferably at least 0.4% sericin by weight of water having a molecular weight of at least 15 kDa and having a proportion of beta-sheet in the secondary structure that exceeds 85%.

The composition of the present invention preferably is a cosmetic product, more preferably a cosmetic product selected from a lotion, a cream, an ointment and a salve.

Another aspect of the present invention relates to a process of preparing a composition as defined herein before, said process comprising:

- providing an aqueous component containing sericin having a proportion of beta-sheet in the secondary structure that exceeds 80%; and
- mixing 100 parts by weight of the aqueous component with at least 5 parts by weight, preferably with at least 10 parts by weight, more preferably at least 20 parts by weight of one or more other components.

Preferably, the aqueous component containing sericin is liquid when it is mixed with the one or more other components. In case the aqueous component contains sericin in a concentration that is sufficient to gel the aqueous component, the aqueous component can be liquefied prior to the mixing and allowed to gel after mixing. This may be achieved by adjusting the pH of the aqueous component to a pH in the range of 4.0 to 5.5 prior to mixing, followed by a pH adjustment to a pH of less than 3.9 or a pH of more than 5.6 after said mixing.

The one or more other components that are mixed with the aqueous component in the present process are preferably selected from the group consisting of fillers, dyes, pH modifiers, solvents, polymers and thickening agents.

According to a particularly preferred embodiment, the process comprises the addition of a water-soluble salt of a multivalent metal cation selected from $Zn^{2+}$, $Cu^{2+}$, $Ca^{2+}$ and combinations thereof.

EXAMPLES

Example 1: Sericin Extraction

Sericin was extracted from *Bombyx mori* cocoons by means of the following procedure:
i) The cocoons were soaked in ultrapure and degassed water at ambient temperature for 15 minutes, with shaking of the contents every 5 minutes. Cocoons were separated from water using forceps.
ii) The prewashed pieces were soaked again in degassed and ultrapure water at 70° C., for 30 minutes (with shaking every 5 minutes). Cocoons were separated from water using forceps.
iii) The cocoons were soaked in ethanol at room temperature for 15 minutes (shaking every 3 minutes). Cocoons were separated from ethanol using forceps.

The cocoons were dried over Whatman filter paper at ambient temperature and atmospheric pressure. The dried cocoons were used as stock material for the extraction process.

Known amounts of water were introduced into containers and heated to 95° C. (using bottom stirred autoclave). Prewashed cocoons (1:30 cocoon to water ratio) were added into the water and the suspensions so obtained were subjected to different extraction regimes.

Sample 1 was kept under stirring and heated to 120° C. for 5 minutes.
Sample 2 was extracted under the same conditions, using an extraction time of 30 minutes.
Sample 3 was also extracted under the same conditions, using an extraction time of 90 minutes.

At the end of the heating period, the heat was turned off and the pressure was released immediately (this allows faster cooling of the slurry).

The sericin was separated from fibroin by centrifugation (6000 rpm (4,000 G) for 30 min) and decanting). The serecin content of the extracts was about 1.1 wt. %.

Molecular weight of the extracted sericin of Sample 1 was determined by SDS-PAGE analysis and found to be between 35 kDa and 250 kDa.

Example 2: Secondary Structure

The secondary structure of the sericin protein in samples 1-3 of Example 1 was analysed using circular dichroism (CD) measurements. Standard CD spectra of protein secondary structures was recorded using 195 to 240 nm wavelength scan and then the data was fitted using online analysis software "K2D3".

A folded protein consists of secondary structures α-helix; β-sheet; loops (linker residues interconnecting secondary structure domains. The software "K2D3" takes 200 to 240 nm as the scan wavelength. The mean residue ellipticity value from Circular dichroism refers to percent of amino acids that contribute to the secondary structures (α-helix & β-sheet) and does not include residues in the linker region. The maximum sum of all secondary structures (46%) was taken from computational model of sericin protein. The sericin beta sheet structure was estimated using results of K2D3 software.

The CD data are presented in terms of mean residue ellipticity (MRE, express as deg $cm^2$ $dmol^{-1}$, as a function of wavelength, using the following equation:

$$[\theta]_{MRE} = \frac{MRW \times [\theta]_{Obs}}{10 \times d \times c}$$

Where $[\theta]_{MRE}$ is the calculated mean residue ellipticity (deg $cm^2$ $mol^{-1}$); MRW, the mean residue weight for the peptide bond [MRW is calculated as $MRW=M/N^{-1}$, where M is molecular mass of the peptide chain (Da) and N is the number of amino acids in the chain]; $[\theta]_{obs}$, the observed ellipticity (expressed in degrees); d, the path length (cm); c, the protein concentration ($gL^{-1}$). All CD spectra were corrected for buffer concentrations and secondary structure were calculated using web based K2D3 analysis tool K2D3: Kelly et al. (2005) *Biochimica et Biophysica Acta* 1751: 119-39. PMID:16027053 neural network software package.

The results of the CD measurements are shown in Table 1.

TABLE 1

| Sample | Extraction time/ minutes | Temperature/ ° C. | % beta-sheet |
|---|---|---|---|
| 1 | 5 | 120 | 92% |
| 2 | 30 |  | 71% |
| 3 | 90 |  | 30% |

Example 3: Rheological Studies

The rheological properties of the sericin extracts of Example 1 were determined by measuring the storage modulus and loss modulus of these extracts (at 25° C.). The results are shown in Table 2.

TABLE 2

| Sample | Sericin concentration (wt. %) | Temperature/ ° C. | Extraction time/ minutes | G' (Pa) | G" (Pa) |
|---|---|---|---|---|---|
| 1 | 1.1 | 120 | 5 | 980 | 120 |
| 2 | 1.1 |  | 30 | 65 | 7 |
| 3 | 1.1 |  | 90 | 5 | 1 |

Hydrogels were formed using different concentrations of Sample 1 of Example 1. The storage modulus and loss modulus of the hydrogels were determined (at 25° C.). The results of these measurement are shown in Table 3.

TABLE 3

| Sericin concentration (% wt.) | G' (Pa) | G" (Pa) |
|---|---|---|
| 0.9 | 104 | 11 |
| 1.3 | 1027 | 97 |
| 1.6 | 3156 | 323 |

Example 4: Rheological Studies in Presence of Metal Ions

Hydrogels containing $Zn^{2+}$ were prepared using Sample 1 of Example 1 and by adding different amounts of $ZnCl_2$.

The storage modulus and loss modulus of the hydrogels were determined. The results of these measurement are shown in Table 4.

TABLE 4

| ppm of $ZnCl_2$ | G' (Pa) | G" (Pa) |
| --- | --- | --- |
| 0 | 114 | 11 |
| 8 | 157 | 16 |
| 25 | 253 | 27 |
| 50 | 433 | 45 |
| 125 | 849 | 117 |

Example 5: Influence of pH

The influence of pH on the storage modulus of a sericin hydrogel was determined using Sample 1 of Example 1. The pH of a 0.9% aqueous solution of sericin was adjusted using HCl (molarity 0.1) or NaOH (molarity 0.1) to provide solutions of different pH.

The storage modulus and loss modulus of the hydrogels were determined. The results of these measurement are shown in Table 5.

TABLE 5

| pH of formulation | G' | G" |
| --- | --- | --- |
| 2.5 | 104 | 19 |
| 3.5 | 260 | 31 |
| 4.5 | Sericin Precipitates | Sericin Precipitates |
| 6.4 | 126 | 12 |
| 7.5 | 149 | 14 |
| 9 | 40 | 4 |

Hydrogel formation occurred at pH<3.5 and between pH 6 to 9.5. No hydrogel formed in the range pH 4 to 5.5.

The invention claimed is:

1. A composition comprising 5 to 100 wt. % of a structured aqueous phase wherein the composition contains 0.1 to 10 wt. % sericin by weight of water, said sericin having a proportion of beta-sheet in the secondary structure that exceeds 90%, wherein the structured aqueous phase has a pH in the range from 2.0 to 4.0 or from 5.5 to 10.5.

2. Composition according to claim 1, wherein the sericin has a molecular weight in the range of 2 kDa to 400 kDa.

3. Composition according to claim 1, wherein the composition contains 0.2 to 4 wt. % sericin by weight of water.

4. Composition according to claim 1, wherein the composition comprises 1 to 80 wt. % of one or more non-aqueous phases and 20 to 99 wt. % of the structured aqueous phase.

5. Composition according to claim 1, wherein the composition comprises at least 0.08 mmol of multivalent metal cation, said multivalent metal cation being selected from $Zn^{2+}$, $Cu^{2+}$, $Ca^{2+}$ and combinations thereof.

6. Composition according to claim 1, wherein the structured aqueous phase comprises a sericin hydrogel.

7. Composition according to claim 1, wherein the structured aqueous phase is a continuous aqueous phase.

8. Composition according to claim 1, wherein the structured aqueous phase contains at least 50 wt. % water.

9. Composition according to claim 1, wherein the composition comprises at least 0.4% sericin by weight of water, said sericin having a molecular weight of at least 10 kDa and having a proportion of beta-sheet in the secondary structure that exceeds 90%.

10. Composition according to claim 1, wherein the composition is a cosmetic product selected from but not limited to a lotion, a cream, an ointment and a salve.

11. A process of preparing a composition according claim 1, said process comprising:
providing an aqueous component containing sericin having a proportion of beta-sheet in the secondary structure that exceeds 90%; and
mixing 100 parts by weight of the aqueous component with at least 5 parts by weight of one or more other components.

12. Process according to claim 11, wherein the one or more other components are selected from selected from the group consisting of fillers, dyes, pH modifiers, solvents, polymers and thickening agents.

13. Process according to claim 11, wherein the process comprises the addition of a water-soluble salt of a multivalent metal cation selected from $Zn^{2+}$, $Cu^{2+}$, $Ca^{2+}$ and combinations thereof.

* * * * *